(12) United States Patent
Lowell (10) Patent No.: US 7,112,332 B1
(45) Date of Patent: Sep. 26, 2006

(54) ORAL OR INTRANASAL VACCINES USING HYDROPHOBIC COMPLEXES HAVING PROTEOSOMES AND LIPOPOLYSACCHARIDES

(75) Inventor: George H. Lowell, Hampstead (CA)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 07/958,426

(22) Filed: Oct. 8, 1992

(51) Int. Cl.
*A61K 39/02* (2006.01)

(52) U.S. Cl. .............. 424/234.1; 424/249.1; 424/250.1; 424/203.1; 424/197.11; 424/193.1; 536/123.1

(58) Field of Classification Search ............ 424/234.1, 424/249.1, 250.1, 203.1, 197.11, 193.1; 536/123.1
See application file for complete search history.

(56) References Cited

U.S. PATENT DOCUMENTS 4,707,543 A * 11/1987 Zollinger et al. ........... 530/402
5,985,284 A * 11/1999 Lowell .................... 424/234.1

OTHER PUBLICATIONS

Black et al. J.Infect.Dis. 1987, 155(6): 1260-1265.*
Cohen et al. J. Infect.Dis. 1988. 157(5): 1068-1071.*
Ruegg et al. J. Immunolog. Methods. 1990. 135: 101-109.*
Formal and Levine, in Bacterial Vaccines (1994), pp. 167-186.
Formal et al., Proc. Soc. Exp. Biol. Med. (1967) 25:347-349.
Herrington et al., Vaccine (1990) 8:353-357.
Keusch and Bennish, in Bacterial Infection of Human (2nd ed.), Evans and Brachman (eds.), New York and London: Plenum Medical (1990), p. 593-620.
Livingston et al., Vaccine (1993) 11(12):1149-1203.
Lowell et al., J. Exp. Med. (1988) 167:658-663.
Lowell et al., Science (1988) 240:800-802.
Mallett et al., Infect. Immun. (1995) 63(6):2382-2386.
Orr et al., American Society for Microbiol. 93rd Gen. Meeting. May 16-20, 1993. Atlanta. E-58 & E59.
Orr et al., Infect. Immun. (1993) 61(6):2390-2395.
Orr et al., Infect. Immun. (1994) 62(11):5198-5200.
Ruegg et al., J. Immunol. Methods. (1990) 135:101-109.
Underdown and Schiff, Ann. Rev. Immunol. (1986) 4:389-417.

* cited by examiner

*Primary Examiner*—Jennifer E. Graser
(74) *Attorney, Agent, or Firm*—Townsend and Townsend and Crew LLP (57) ABSTRACT

An immunogenic complex, essentially consisting of neisserial outer membrane protein proteosomes hydrophobically complexed to native purified bacterial lipopolysaccaride and formulated in accordance with the current invention for mucosal delivery such as via the oral or intranasal route is used as a vaccine. Specifically, a vaccine using *shigella* lipopolysaccharides complexed to proteosomes for such mucosal administration induces IgG and IgA antibodies in sera and in respiratory and intestinal fluids. Furthermore, such antibodies are associated with protection against shigella infection and these vaccines are herein demonstrated to protect against mucosal infection with shigella.

20 Claims, 5 Drawing Sheets

Protein (solid) and LPS (dashed) levels in fractions eluted from CL-4B column. (A) Proteosome-LPS complex, (B) native S.f.2a LPS.

Table 1

| Route | Intranasal imm. | | Oral imm. | |
|---|---|---|---|---|
| Processing | 2hrs | 1hr | 2hrs | 1hr |
| Vaccine | 0.2 O.D. | 0.5 O.D. | 0.2 O.D. | 0.5 O.D. |
| LPS | 22 | < 6 | < 6 | < 6 |
| Prot-LPS | 4829 | 1837 | 1166 | 527 |
| LPSad | < 6 | < 6 | < 6[1] | < 6[1] |
| Prot-LPSad | < 6 | < 6 | 57.4[1] | 14.1[1] |

[1] 3 doses of vaccine (0, 1 and 4 weeks).

Serum IgG levels in mice as determined by ELISA. Mice were immunized with two doses of vaccine at 0 and 3 weeks. Data are expressed as the average maximal dilution which gave at least the specified O.D.

*FIG. 4*

HOMOLOGOUS PROTECTION AGAINST SHIGELLA FLEXNERI KERATOCONJUNCTIVITIS (SERENY TEST) IN GUINEA PIGS BY INTRANASAL OR ORAL IMMUNIZATION WITH PROTEOSOME-LPS VACCINES
(Challenge dose = 100-260 million bacteria per eye)

| Guinea Pig Group | Route of Immunization | Proteosome-LPS Vaccine (ug/dose x #) | INFECTION (# / Total) | | | PROTECTION (%) | | |
|---|---|---|---|---|---|---|---|---|
| | | | None | Mild | Severe | Full (only) | Partial (only) | Combined (Full + Partial) |
| a | Nasal | 20 ug x 2 | 0/4 | 1/4 | 3/4 | 0% | 25% | 25% |
| | Oral | 100 ug x 2 | 4/6 | 0/6 | 2/6 | 67% | 0% | 67% |
| | Oral | Saline Control | 0/4 | 0/4 | 10/10 | 0% | 0% | 0% |
| b | Nasal | 20 ug x 3 | 2/4 | 2/4 | 0/4 | 50% | 50% | 100% |
| | Oral | 100 ug x 3 | 4/4 | 0/4 | 0/4 | 100% | 0% | 100% |
| | Oral | Saline Control | 0/4 | 0/4 | 4/4 | 0% | 0% | 0% |
| c | Nasal | 20 ug x 4 | 2/9 | 7/9 | 0/9 | 22% | 78% | 100% |
| | Oral | 100 ug x 4 | 1/6 | 2/6 | 3/6 | 17% | 33% | 50% |
| | Oral | Saline Control | 0/5 | 0/5 | 5/5 | 0% | 0% | 0% |
| TOTAL (a & b) | Nasal | 20 ug x 2 or 3 | 2/8 | 3/8 | 3/8 | 25% | 38% | 62% |
| | Oral | 100 ug x 2 or 3 | 8/10 | 0/10 | 2/10 | 80% | 0% | 80% |
| | Oral | Saline Control | 0/14 | 0/14 | 14/14 | 0% | 0% | 0% |
| TOTAL (a, b, & c) | Nasal | 20 ug x 2, 3, or 4 | 4/17 | 10/17 | 3/17 | 24% | 59% | 82% |
| | Oral | 100 ug x 2, 3, or 4 | 9/16 | 2/16 | 5/16 | 56% | 13% | 69% |
| | Oral | Saline Control | 0/19 | 0/19 | 19/19 | 0% | 0% | 0% |

*FIG. 5*

ORAL OR INTRANASAL VACCINES USING HYDROPHOBIC COMPLEXES HAVING PROTEOSOMES AND LIPOPOLYSACCHARIDES

GOVERNMENT INTEREST

The invention described herein may be manufactured, licensed and used by or for governmental purposes without the payment of any royalties thereon.

BACKGROUND OF THE INVENTION

Shigella flexneri and other Shigella species represent a major cause of diarrheal diseases in developing countries (Keusch, G. T. and M. L. Bennish. 1991. in Evans AS and Brachman PS ed. Bacterial Infection of Human $2^{nd}$ ed. New York and London: Plenum Medical p. 593.). It has been shown that type specific protection against shigellosis can be acquired in man after infection with a wild type or attenuated bacteria (Cohen, D. et al. 1988. J. Infec. Dis. 157: 1068.; Herrington, D. A. et al. 1990. Vaccine. 8:353; Black, R. E. et al. 1987. J. Infect. Dis. 155:1260.) and there is direct evidence that anti-type-specific LPS antibodies are associated with this protection (Cohen, D. et al. 1988. J. Infec. Dis. 157:1068.; Black, R. E. et al. 1987. J. Infect. Dis. 155:1260). It is widely agreed that local mucosal immune responses, especially secretory immunoglobulins including IgA and IgG play a major role in protection against such mucosal enteric pathogens following mucosal immunization or natural exposure; serum levels of these antibodies may be a measure or marker reflecting the production of local antibodies and, as such, may also indicate or contribute to protection (Underdown, B. J. and J. M. Schiff. 1986. Ann. Rev. Immunol. 4: 389–417; Cohen, D. et al. 1988. J. Infec. Dis. 157:1068.).

Since the demonstration in 1967 (Formal, S. B. et al. 1967. Proc. Soc. Exp. Biol. Med. 25: 347–349) that parenteral immunization with live or killed shigella bacteria was ineffective in protecting against oral challenge or monkeys with shigella, the major thrust of research has focused on the use of live attenuated or genetically constructed vaccines (Formal, S. B. and M. M. Levine. in Bacterial Vaccines, pp. 167–186). The problems associated with development of successful live vaccines include the narrow window between efficacy and safety of such vaccines since their ability to cause disease and side effects can be exceedingly dose dependant. The novelty of the current approach is emphasized by the fact that results of immunogenicity and protection in established animal models of disease were achieved despite using a sub-unit, non-living vaccine delivery system that is safe for intranasal or oral delivery. While several other approaches to the problem of development of oral or intranasal vaccines to protect against mucosal diseases in the gastro-intestinal or respiratory tract have been explored, none uses the technology of the instant invention; nor have they been effective in demonstrating induction of high levels of IgA and IgG in both mucosal secretions and sera as well as protection in established animal models as is here shown.

The data herein disclosed show that the instant invention can be used as an oral or intranasal non-living sub-unit vaccine to protect against mucosal diseases of the gastro-intestinal tract such as shigellosis. In addition, since high antibody levels are induced in either the respiratory or gastro-intestinal tracts following either oral or intranasal immunization, and since protection is shown against either conjunctival or respiratory challenge, these vaccines can also be used to protect against diseases that enter the body via respiratory, ocular or gastro-intestinal routes. By logical extension of the well-known common mucosal immune system, these vaccines also will result in protection against mucosal diseases of the urogenital and auditory tracts.

Proteosomes have previously been used with peptides (U.S. patent application Ser. No. 07/642,093 filed Jan. 16, 1991 which is a Continuation of 07/065,440 filed Jun. 23,1987) and large proteins (U.S. patent application entitled "Immunopotentiating System for Large Proteins and Polypeptides" Ser. No. 07/336,952, filed 12 Apr. 1989) in vaccine development of parenteral vaccines and Zollinger et al. (U.S. Pat. No. 4,707,543; Nov. 17, 1987) have used meningoccocal outer memebrane proteins non-covalently complexed to detoxified lipopolysaccharides or polysaccarides in parenteral vaccines. The Zollinger work, however, specifically teaches away from the instant invention since the thrust of their work emphasizes that detoxified LPS or polysaccharide can be used wheras in the instant invention, detoxified LPS, in direct contrast to the non-detoxified LPS, is entirely ineffective. Furthermore, Zollinger neither showed, claimed nor suggested that his vaccines would be effective when deliverd via the oral or intranasal route.

SUMMARY OF THE INVENTION

It is an object of the present invention to provide a novel vaccine delivery system using proteosomes hydrophobically complexed to lipopolysaccharides and formulated for oral or intranasal administration to induce protective antibodies in sera and/or respiratory and/or intestinal secretions that are associated with protection against disease.

In accordance with the invention, vaccines using Shigella flexneri 2a or Shigella sonnei lipopolysaccharide (LPS) induce anti-LPS antibodies in the aformentioned fluids and protect against homologous shigella infection in a well-known animal model of shigellosis.

DETAILED DESCRIPTION

LPS Preparation

LPS was extracted by hot phenol from single isolate of *Shigella flexneri* 2a or *Shigella sonnei* (Westphal, O. and K. Jann. 1965. Carbohydr. Chem. 5:83.11). The LPS extraction protocol was generally as follows:

Grow bacteria in LB for 2–3 hrs at 37° C. Incubate 3 ml starter in rho-bottles with nutrient agar (+2% agar), overnight at 37° C. Harvest bacteria with 15 ml saline/bottle (+glass beads) and filter the suspension through gauze pad. Centrifuge the filtrate at 5000 RPM, 4° C., (Sorval RC5B, 250ml tubes, cat. 03937 in GSA rotor) for 15 minutes and resuspend the pellet in ⅕5 ml saline/Tube.

Add acetone to the resuspended bacteria (1.5 L/10 ml resuspended bacteria) and left for two days. Remove the Acetone by filtration through Whatman paper under vacuum and dry the bacteria completely under vacuum to form white, fine powder. Add $dH_2O$ to the powder (25 ml/1.4 gr dried bacteria) and gently steer until all powder is hydrated. Add phenol (at 37° C.) to the mixture (1:1 w/w) and agitate gently in 68° C. preheated water bath for 10 min. Cool the mixture in ice and centrifuge at 3000 RPM, 4° C., (30 ml tubes, cat. 03163 in GSA rotor) for 30 min. Gently collect the upper phase (water phase) and add cold $dH_2O$ (0.5 volume of the collected upper phase) to the lower phase and mix well. Centrifuge as in #9, collect upper phase and combine the two upper phases.

Reextract the combined upper phases as in #8–#11. Dialyze against $H_2O$ for two days (15 K dialyzis bag) with at least two water exchanges. Centrifuge at 10000 RPM, 4° C. (30 ml tubes, cat. 03163 in GSA rotor) for 30 minutes and collect supernatant. Add absolute ethanol (ethanol/supernatant 10:1 v/v) and leave for two days at 4° C. Centrifuge at 10000 RPM, 4° C. (250 ml tubes, cat. 03937 in GSA rotor) for 2 hrs, discard supernatant and resuspend pellet in ¼10 ml $dH_2O$ Dialyze against $dH_2O$ in 15 K dialyzis bag for two days. Freeze dry.

Alkaline detoxified LPS (LPSad) was prepared using mild alkaline treatment (Skidmore, B. J. et al. 1975. *J. Immunol.* 114:770). This alkaline-detoxified LPS was ineffective in the system.

Proteosome Preparation

Outer membrane proteins from group B serotype 2b *N. meningitides* were extracted with detergent as follows:

1.0 PREPARATION OF BACTERIAL PASTE

Dissolve lyophilized ampule of group C type 2 Meningococci in d.w.

Plate on petri plates of Neisseria selective media overnight in $CO_2$ incubator or candle jar at 37° C. Suspend swab full of isolated colonies in 150 ml Modified Watson-Sherp liquid media in a 1000 ml ehrlenmeyer. For 30 liters final culture, need to start with eighteen (18) 1000 ml ehrlenmeyers each containing 150 ml media so that total media volume in 18 1000 ml ehrlenmeyers is 2.7 liters.

Grow 4 hrs at 37° C. in a shaking incubator. Transfer each 150 ml of this 4 hr growth to 1.5 liter media (i.e. 1:11 dilution) in a 5 liter fernbach (or ehrlenmyer) so that each 5 liter vessel contains a total 1.65 liters.

Eighteen vessels have a total of 30 liters. Therefore, alternatively, at this point, can use 30-liter fermenter. Expect 0.8–1.0 gms final material (outer membrane protein proteosome vesicles) per 30 liters. Four such runs or one 120 liter fermenter would therefore yield 3.2–4.0 gms protein. Grow 24 hrs with good aeration at 37° C. in a shaking incubator to late log phase but not stationary phase. Sample growth to verify purity of culture by: a) plating on non-selective plates (Mueller-Hinton) for 24 hr growth and b) gram stain. Add 0.5% phenol (5 cc/liter of 90%). Let sit for 1 hr. to kill bacteria. Centrifuge as fast as possible (4–10,000 g) for 40 min (9,000 RPM sorval GS3). Wash x1 in NS in 1/5culture volume and spin in weighed culture bottles. Record lot number and amount of paste per bottle and total weight of paste: Freeze at −20° C. until ready for extraction.

2.0 EXTRACTION OF OUTER MEMBRANE VESICLES FROM KILLED CELLS: ETHANOL PRECIPITATION 2.1 Area cleaned, cleared and ready for use.

2.2 Thaw cells at room temperature (if frozen) and Record lot nos. and amount of killed cell paste used:

2.3 Suspend cells in 1 M Sodium Acetate buffer, pH 5.0 using 1 ml per gram of cells.

2.4 Mix the suspension in a Waring type blender for 15 sec. at low speed at 22–25° C.

2.5 Add d.w. at 22–25° C.: 1.5 ml d.w. per ml of suspension from step 2.3.

2.55 Mix: form an even suspension; measure volume in a graduated cylinder:

2.6 To the combined volume from step 2.55 in a beaker, add an equal volume of the extraction solution 1.0 M Calcium Chloride/Empigen 6.0%.

2.65 Stir mixture at 22–25° C. for 1 hour on a magnetic mixer.

2.7 FIRST ETHANOL ADDITION calculation (rounded to nearest 0.1 ml) to yield final concentration of 20% ethanol vol/vol): Amount of Ethanol added=(combined total volume from step 2.6)(0.25):

2.8 Add calculated volume from step 2.7 of absolute Ethanol to the suspension from step 2.65 and stir on magnetic stirrer for 15 min. at 22–25° C.

2.9 Centrifuge the suspension from step 2.8 at 17,800×g for 10 min. at 1–5° C. (10,000 rpm using the Beckman JA-10 rotor or equivalent)

2.95 Pour the supernatant thru clean cheesecloth and recover filtrate.

2.10 SECOND ETHANOL ADDITION calculation (rounded to nearest 0.1 ml) to yield final concentration of 45% ethanol vol/vol): Amount of Ethanol added=(combined total volume from step 2.95)(0.45):

2.11 Add calculated volume from step 2.1 of absolute Ethanol to the suspension from step 2.95 and stir on magnetic stirrer for 15 min. at 22–25° C.

2.12 Centrifuge suspension from step 2.11 at 17,800×g for 10 min. at 1–5° C. (e.g. using the Beckman JA-10 rotor at 10,000 rpm or equivalent) as in step 2.9; pour off and discard supernatnant.

3.0 PREPARATION OF OUTER MEMBRANE VESICLES (OMV): EXTRACTION WITH TEEN 1.0%:

3.1 FIRST TEEN 1.0% EXTRACTION: Resuspend the pellets from step 2.12 with 1.5 ml TEEN 1.0% buffer per gram extracted cell paste used in step 2.2.

3.2 BREAK UP pellets with a spatula. Transfer aliquots of suspension to Dounce Teflon Homogenizer and gently crush pellets until all material is a fine suspension.

3.3 With a sterile 21 gauge needle on a 50 cc syringe, aspirate and release suspension into beaker to create finest suspension and then stir on magnetic stirrer for 15 min. at 22–25° C.

3.4 SONICATE the suspension in a Branson Sonication Bath model 5200 starting at 19–25° C. using 200 ml solution per batch in a 600 ml beaker for 15 min. or 500 ml solution in a 1000 ml beaker as needed.

3.5 Centrifuge the sonicated solution from step 3.4 at 27,500×g (13,000 rpm) for 25 min. in Beckman JA-14 rotor or equivalent at 1–5° C. Carefully recover supernatants, pool and store at 1–5° C. SAVE pellets for second extraction.

3.6 SECOND TEEN 1.0% EXTRACTION: Resuspend the pellets from step 3.5 using one-half the volume used in step 3.1.

3.7 BREAK UP pellets using spatula, Dounce HOMOGENIZATION, and SONICATION as in steps 3.2–3.4. CENTRIFUGE as in step 3.5; RECOVER SUPERNATANTS and SAVE PELLETS for Third extraction.

3.8 THIRD TEEN 1.0% EXTRACTION: Resuspend the pellets from step 3.7 using one-Third the volume used in step 3.6.

3.9 BREAK UP pellets using spatula, Dounce homogenization, and sonication as in steps 3.2–3.4. CENTRIFUGE as in step 3.5, RECOVER SUPERNATANTS and SAVE PELLETS (if substantial) for Extra extraction to repeat as in step 3.8.

3.10 COMBINE the first, second and third pooled supernatants from steps 3.6, 3.8 and 3.10, and Remove two 3 ml samples for analyis including Average protein determinations (by Lowry and Bradford).

3.11 CONCENTRATE to about 50% of volume to yield protein of at least 4.0 mg/ml using Amicon filtration system (3 atmos.). Remove two 3 ml samples for analysis. Concentrated protein determinations:

3.12 Material is stored at 1–5° C. if further processing to start within 24 hrs.

If not, store at −20° C.

4.0 REMOVAL OF ENDOTOXIN FROM OMV: PART A: AMMONIUM SULFATE PRECIPITATION 4.1 Obtain and, if necessary, thaw, material from step 3.13.

4.2 FIRST AMMONIUM SULFATE addition added at 500 g per liter solution.

4.3 STIR to dissolve at 19–25° C. and let stand at same temperature for 15 minutes.

4.4 CENTRIFUGE in plastic centrifuge bottles at 20,000×g (11,100 rpm in sorval GSA rotor or 11,500 in Beckman JA 14 rotor) or equivalent for 20 min. at 1–5° C.; discard supernatants.

4.5 DISSOLVE the pellets in TEEN 1.0% buffer using one-quarter the volume used in step 4.2 magnetically stirring at 1–5° C.

4.55 MEASURE Protein content: Adjust to 2–3 mg/ml: add TEEN 1.0% solution (if turbid, LPS not removed; if <2.0 mg/ml protein lost).

4.6 STIR at 19–25° C. with magnetic stiring bar for one hr.

4.65 SONICATE in a Branson Sonication Bath model 5200 or equivalent for 15 min. at 19–25° C. using 200 ml solution per batch in a 600 ml beaker or 500 ml solution in a 1000 ml beaker as appropriate.

4.7 SECOND AMMONIUM SULFATE addition: to combined sonicated batches, ADD 500 g per liter of solution as in step 4.2:

4.8 STIR and CENTRIFUGE at 20,000×g as in steps 4.3 and 4.4.

4.9 DISSOLVE pellets using TEEN 1.0% buffer using 85% of "New volume" used in step 4.55 stirring at 1–5° C.

4.10 STIR and SONICATE as in steps 4.6 and 4.65.

4.11 THIRD AMMONIUM SULFATE addition: to combined sonicated batches, ADD 500 g per liter of solution as in step 4.2:

4.12 STIR and CENTRIFUGE at 20,000×g as in steps 4.3 and 4.4.

5.0 REMOVAL OF ENDOTOXIN FROM OMV: PART B: TEEN 1.0% EXTRACTION 5.1 FIRST TEEN 1.0% EXTRACTION: Dissolve pellets in TEEN 1.0% buffer using 60% of the "New volume" used in step 4.55 stirring at 1–5° C.

5.2 SONICATE as in step 4.65.

5.3 CENTRIFUGE the sonicated solution from step 5.2 at 27,500×g for 25 min. at 1–5° C. (13,000 rpm in a Beckman JA-14 rotor or equivalent). Carefully RECOVER SUPERNATANTS, pool and store at 1–5° C. SAVE pellets for second extraction.

5.4 SECOND TEEN 1.0% EXTRACTION: Dissolve the pellets from step 5.3 using 30 ml of TEEN 1.0% buffer per 250 ml centrifuge bottle stirring at 1–5° C.

5.5 BREAK UP pellets using spatula, Dounce homogenizer, syringe and sonication as in steps 3.2–3.4.

5.6 CENTRIFUGE as in step 5.3. Recover supernatants and SAVE pellets for Third extraction.

5.7 THIRD TEEN 1.0% EXTRACTION: Resuspend the pellets from step 5.6 using 25 ml of TEEN 1.0% buffer per 250 ml centrifuge bottle stirring at 1–5° C.

5.8 BREAK UP pellet using spatula, Dounce homogenizer, syringe and sonication as in steps 3.2–3.4. CENTRIFUGE as in step 5.3, RECOVER SUPERNATANTS, pool and store at 1–5° C.

5.9 COMBINE the FIRST, SECOND and THIRD pooled supernatants from steps 5.3, 5.7 and 5.8, and measure the total volume:

5.10 DIALYZE this solution vs. TEEN 0.1% buffer with Spectrapor #3787-D42 dialysis tubing (12,000 MWCO) for 40–44 hrs. at 1–5° C. with two buffer changes. Buffer/to solution volume ratios mus be at least 10:1.

5.11 RECOVER THE RETENTATE and SAVE; measure and record the volume. Remove two 2.5 ml samples for analyis including Average protein determinations (by Lowry and Bradford).

5.12 ALIQUOT into 5 ml vials, label and store at −70° C. Label "N. mening. Gp. B tp 2 OMP PROTEOSOMES" with lot no. and date. Remove two 2.5 ml samples for analyses: SDS-PAGE, LPS and nucleic acid.

Vaccine Preparation

LP-S or LPSad from *Shigella flexneri* 2a or *S. sonnei* and group B serotype 2b *Neisseria meningitides* outer membrane proteins were mixed at 1:1 ratio (w/w) in 1% Empigen (2 mg/ml final concentration of LPS/LPSad and protein). The mixture was dialyzed in 1000 DALTON molecular weight cutoff (MWCO) dialyzis bags against PBS at 4° C. for 10 days with daily buffer exchanges versus PBS or Tris saline buffer or their equivelant. Since both the proteosomes and the LPS are of very high molecular weight, it is obviously likely that dialysis membrane with MWCO of far greater than 1000 daltons can reasonably be used and similarly, the length of the dialysis time would be considerably shortened. The vaccine preparations, prot-LPS or prot-LPSad were kept at 4° C. and diluted to the specific concentration with PBS just prior to vaccination.

METHODS USED IN ANALYSIS OF VACCINE COMPLEX

CL-4B Column

Samples of vaccine preparation were eluted through CL-4B column (2.5×40 cm) and fractions were collected. The various fractions were assayed for protein by the Bradford method (Bradford, M. M. 1970. *Anal. Biochem.* 72:248.) with BSA as standard. The LPS level in each fraction was calculated by competition ELISA as follows: 100 ul samples from each column fraction were incubated with 300 ul of specific-LPS-positive guinea-pig serum diluted 1:150 in filler for 1 hr, 37° C. Homologous LPS samples ranging from 100 ìg/ml to 3.125 ìg/ml were incubated as standards. The incubated serum and samples or standards were placed in LPS-precoated and blocked 96 wells plates for 2 hrs, 37° C. and the plates were developed as described under ELISA. The LPS level in each fraction was calculated with the standard curve obtained from the LPS standards.

METHODS USED IN ANALYSIS OF VACCINE IMMUNOGENICITY AND EFFICACY

Immunization

1) Mice: balb\c, age 7–10 weeks, 4–5 per group were immunized with the specific antigens either orally or intranasally. Orally (P.O.): 100 ul PBS, 0.2 M NaHCo$_3$ containing 100 ìg LPS/LPSad or 200 ìg prot-LPS/LPSad complex. Intranasally (I.N.): 25 ul PBS containing 10 ìg LPS/LPSad or 20 ug prot-LPS/LPSad complex. Mice were anaesthetized prior to intranasal immunization. Four vaccine preparation were used: LPS, LPSad, prot-LPS, prot-LPSad. A control group was vaccinated with PBS, 0.2 M NaHCO$_3$ (P.O.) or PBS (I.N.). The vaccines were given in four different protocols: (a) one dose (b) two doses one week apart, (c) two doses three week apart, and (d) three doses one and three weeks apart.

2) Guinea pigs: DH guinea pigs age 2–3 month were immunized with prot-LPS administrated either orally or intranasally. Orally: 200 ul PBS, 0.2 M NaHCO$_3$ containing 200 ug prot-LPS complex or intranasally: 50 ul PBS containing 40 ug prot-LPS complex. The animals were aneasthesized in both cases.

Antibody Sampling

1) Mouse lung wash: 9–11 days after the last immunization mice were sacrificed by CO$_2$ suffocation and lungs exposed. A canula was inserted into the trachea and using three-way stopcock, lungs were washed with 2 ml PBS, 0.1% BSA and wash fluids were collected.

2) Mouse intestinal wash: Following the lung wash, the small intestine was removed and 2 ml PBS, 0.1% BSA, 50 mM EDTA and 0.1 mg/ml soybean trypsin inhibitor were passed through and collected. PMSF (1 mM final concentration) was added to the intestine wash after collection. Both lung and intestine washes were vortexed vigorously and centrifuged to remove cells and debris, the supernatents were collected and kept at –20° C. until assayed.

Serum preparation: Sera were prepared. from blood collected from the killed mice and kept at –20° C. until assayed. Blood from guinea pigs was collected via cardiopuncture under anaesthetization, serum was separated and kept at –20° C. until assayed.

ELISA: The antibody level in the various extracts e.g. serum, intestinal wash and lung wash was determined as described (2). Briefly, 96 wells flat bottom high binding plates (Costar, Cambridge, Mass., US) were precoated with the specific LPS, blocked with BSA/casein and washed three times. Serially double diluted samples in blocking solution were incubated in the plates and after the incubation period, the plates were washed three times and alkaline-phosphatase conjugated anti-guinea pig or anti-mouse IgG/IgA diluted 1:1000 (Sigma, St. Louis, Mo., US) was added. plates were then washed three times, substrate was added and the absorbance at 405 nm was detected. The antibody titer is expressed as the maximal dilution which gave an O.D. equal or above the indicated value after specific processing period.

Challenge in guinea pigs (Sereny test): Based on the standard challenge assay for the pathogenesis of shigellosis (Sereny, B. 1957. *Acta Microbiol. Acad. Sci. Hung.* 4:367; Hartman, B. A. et al 1991. *Infec. and Immunol.* 59:4075.), the conjunctival sac of one eye of the animal was inoculated with 30 ìl suspension containing about $1 \times 10^8$ bacteria and the eye lids were lightly massaged. Two to three days after inoculation, the eyes were screened for the level of keratoconjunctivitis developed.

RESULTS OF VACCINE ANALYSIS, IMMUNOGENICITY AND EFFICACY

Complex Efficiency

Figure 1:
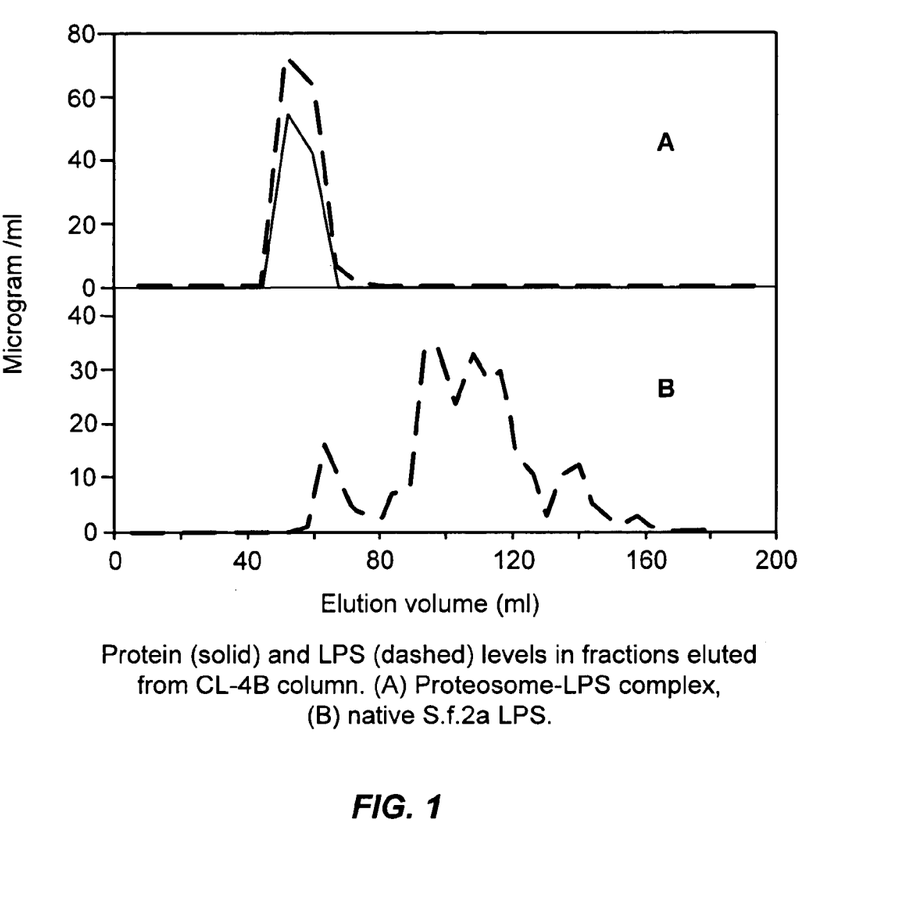
FIG. 1 is a graph depicting Protein (solid) and LPS (dashed) levels in fractions eluted from CL-4B column. (A) proteosome-LPS complex, (B) native S. flexneri 2a LPS.

FIG. 1 shows the protein and LPS patterns as measured after fractionation with CL-4B column. It is demonstrated that in the case of proteosome-LPS complex, the LPS and the proteosomes were detected at the same fractions at the void volume of the column (FIG. 1A). On the other hand, native LPS eluted much slower, thus, easily differentiated from complexed LPS (FIG. 1B).

Immunogenicity in Mice

Figure 2:
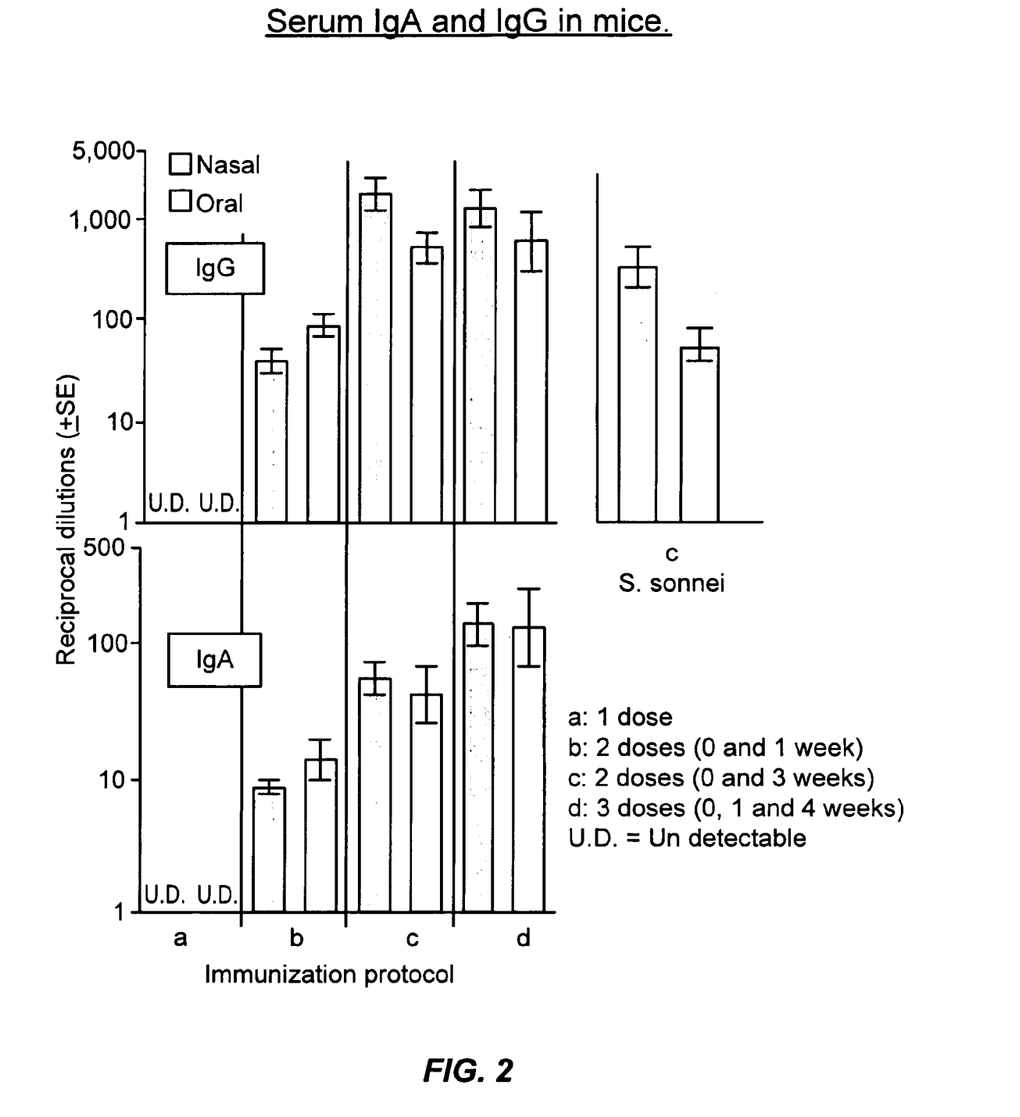
FIG. 2 is a graph depicting Serum IgG and IgA in mice as determined by ELISA. Mice were immunized either orally or intranasally with prot-LPS complex using S. flexneri 2a LPS or S. Sonnei LPS. The results are expressed as the maximal reciprocal dilution which gave an O.D. greater than 0.5 after 1 hr (IgG) or 0.2 after 2 hrs (IgA) processing with substrate.
Figure 3:
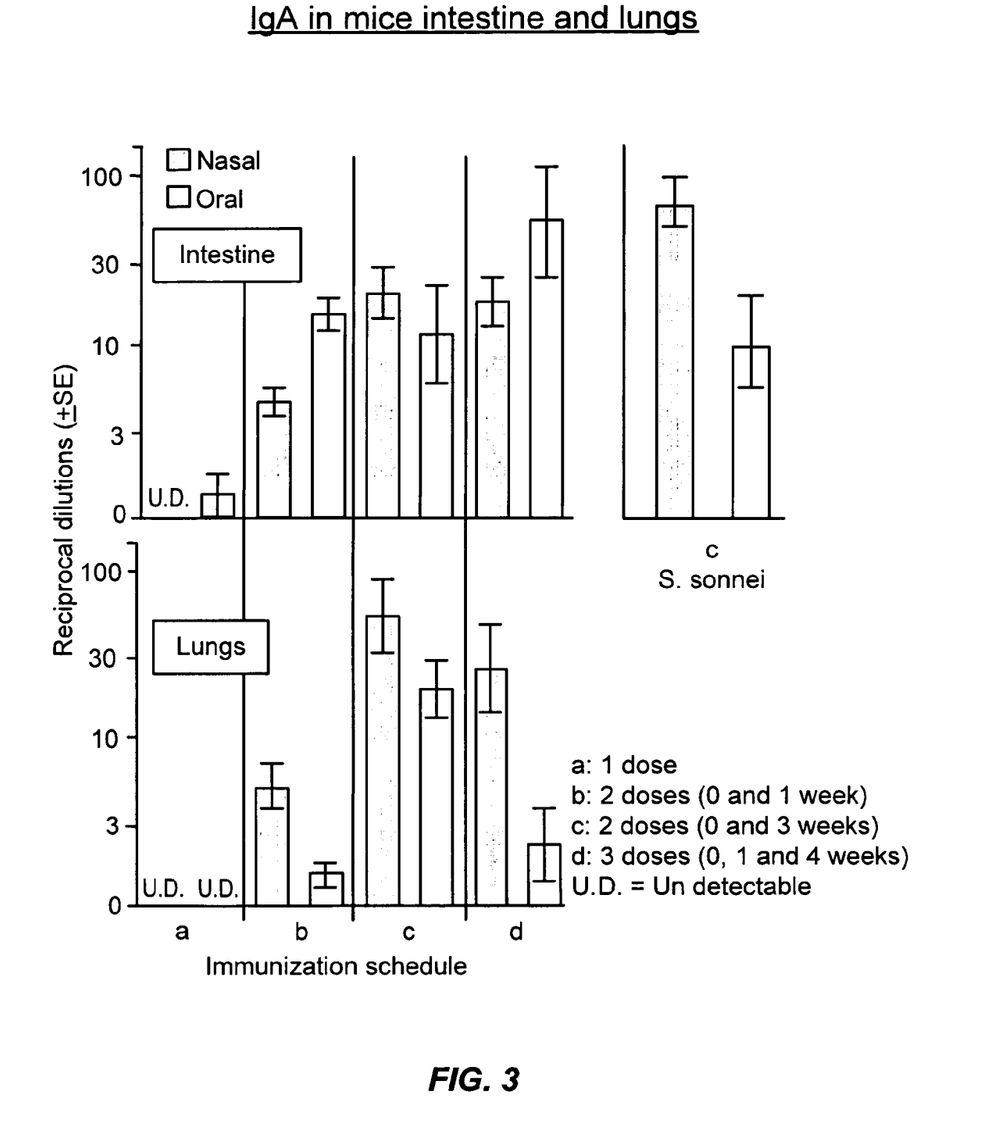
FIG. 3 provides Intestinal and lung IgA in mice as determined by ELISA. Mice were immunized either orally or intranasally with prot-LPS complex using S. flexneri 2a LPS or S. Sonnei LPS. The results are expressed as the maximal reciprocal dilution which gave an O.D. greater than 0.5 (intestine) or 0.2 (lungs) after 2 hrs processing with substrate.
Figure 4:
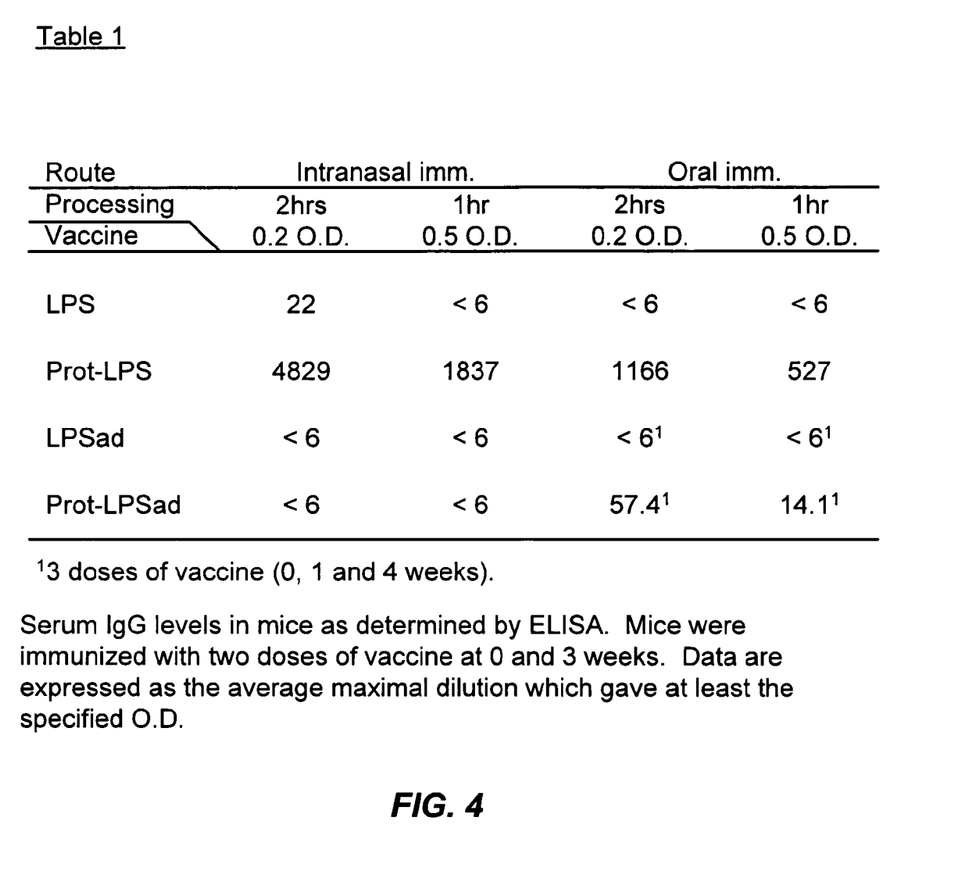
FIG. 4 depicts Table 1 of serum IgG levels in mice as determined by ELISA. Mice were immunized with two doses of vaccine at 0 and 3 weeks. Data are expressed as the maximal reciprocal dilution which gave at least the specified O.D.

9–11 days after the last immunization, serum and secretions from intestines and lungs were collected and the specific antibody level was measured in ELISA. Proteosome-LPS complex has a remarkable advantage as compared to LPS, LPSad or prot-LPSad complex in inducing antibody production against *Shigella flexneri* 2a LPS in the serum (FIG. 4, Table 1). Indeed, the inability of LPS alone, or even alkaline-detoxified LPS complexed to proteosomes (prot-LPSad) to give significant antibody levels emphasizes the remarkable specificty of the instant invention since only the native LPS complexed to proteosomes (Prot-LPS) was effective. Similar data were obtained with proteosomes complexed to LPS from *S. sonnei*. The LPS-specific antibody titer in serum of mice immunized with Proteosome-LPS complex after one, two or three doses of vaccine (FIG. 2) shows that the highest levels of IgA or IgG were achieved when the vaccine was given at 2 doses, 3 weeks apart or in 3 doses. In most cases, one dose of vaccine failed to elicit any detectable antibody levels in the serum as measured by ELISA after 1 hr incubation with the substrate. Longer incubation periods show induction of antibody production by the proteose-LPS complex even after one dose of vaccine (data not shown). There was no relative advantage to oral or intranasal routes in terms of serum antibody levels (FIG. 2). The specific anti-*S.flexneri* 2a LPS IgA levels in mice intestine shows a good correlation to the response observed in the serum in terms of the dose dependency and the lack of differences between oral and intranasal immunization (FIG. 3). Similar data was obtained using *S. sonnei* LPS complexed to proteosomes. In lungs however, intranasal immunization was more efficient in eliciting anti-*S.flexneri* 2a LPS IgA as compared to oral immunization (FIG. 3). Using *S. sonnei* LPS complexed to proteosomes, lung antibody levels were good using both routes.

Challenge in Guinea Pigs

Figure 5:
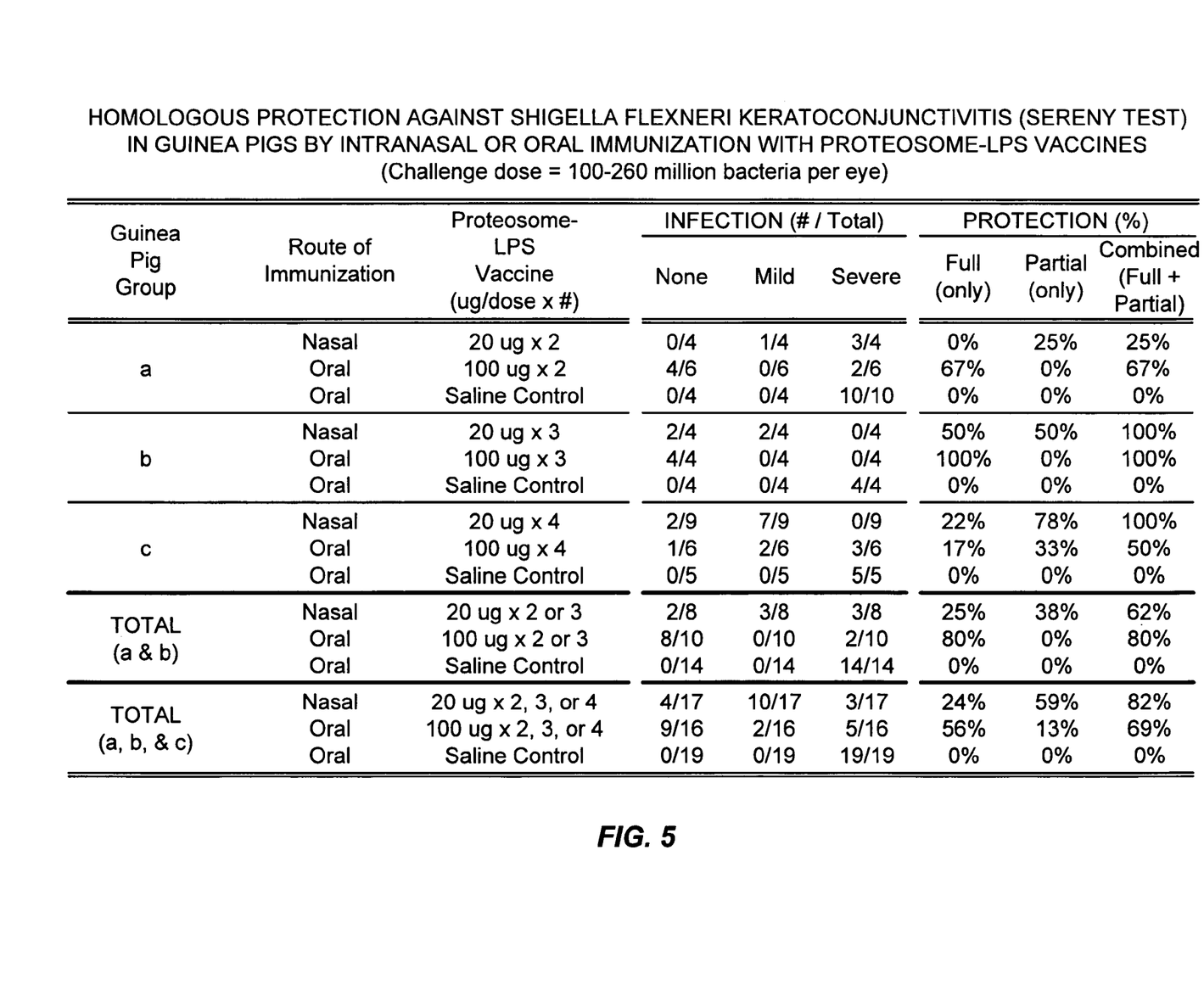
FIG. 5 depicts Table 2 providing results of three challenge experiments in guinea pigs (Sereny test) wherein the animals were vaccinated with two doses at 0 and 3 weeks (group 1), three doses at 0,1 and 3 weeks (group 2) or 4 doses.

Following the results obtained with mice which emphasized the necessity of a booster dose, we vaccinated three groups of guinea pigs with prot-LPS preparation, all three groups were vaccinated either orally or intranasally. The first group was vaccinated with two doses of vaccine at 0 and 3 weeks and the second group was vaccinated with three doses at 0,1 and 3 weeks. 12–14 days after the last vaccination, the guinea pigs were challenged (sereny test) with 30$\mathring{1}$1 PBS containing 7.6×10$^7$ (group 1), 1×10$^8$ (group 2) or 2.6×10$^8$ (group 3) *S. flexneri* 2a (E22). Two or three days after the challenge, the animals were examined for keratoconjunctivitis. The animals could be sub-divided into three sub-groups upon the severity of infection observed. The results obtained in the sereny tests (FIG. 5) shows clearly that the prot-LPS complex was able to elicit in vivo protection against the homologous bacteria. The combined results shows that after intranasal immunization, 14 out of 19 animals were at least partially protected ($p<0.001$). After oral immunization, 11 out of 16 were at least partially protected ($p<0.001$) and 9 out of 16 were completely protected ($p<0.001$). All animals in the control groups (16 out of 16) were completely unprotected.

Similar experiments performedusing *S. sonnei* LPS complexed to proteosomes showed that whereas 80% (e.g. 8 out of 10) guinea pigs were infected in control groups (Sereny test), 70% to 80% of guinea pigs immunized with two doses of *S. sonnei* LPS complexed to proteosomes were protected in three separate experiments. In these experiments, proteosomes from two different sources were used emphasizing the reproducibility of the vaccine. In addition, in the respiratory model of shigella infection developed by L. Hale et al, 90% (9 out of 10) swiss outbred mice challenged with shigella intranasally died whereas 75% (6 of 8) mice immunized orally twice with 100 ug of *S. sonnei* complexed to proteosomes survived thus confirming the efficacy of the vaccine even when challenged to induce death by respiratory infection.

Data from mice immunized with either the *S.flexneri* 2a or *S. sonnei* vaccines immunized either orally or intranasally also showed high levels of anti-meningococcal protein antibodies in sera, intestinal secretions and lung washes indicating the applicabilityh of these vaccines to protect against meningococcal diseases as well.

What is claimed is:

1. An oral or intranasal subunit nonliving vaccine comprising a carrier and an effective amount of an immunogenic hydrophobic complex essentially consisting of proteosomes and at least one non-detoxified antigenic lipopolysaccharide, wherein the effective amount is sufficient, upon being administered orally or intranasally, to protect against infectious or toxic diseases entering at mucosal surfaces.

2. The vaccine according to claim 1 wherein the bacterial polysaccharide is from gram negative bacteria.

3. The vaccine according to claim 1 including an antigen complexed to proteosomes is from other microorganisms.

4. The vaccine according to claim 1 wherein the proteosomes are derived from *N. meningiditis*.

5. The vaccine according to claim 1 wherein the proteosomes are derived from *N. gonorrhea*.

6. The vaccine according to claim 2 wherein the gram negative bacteria is selected from *Shigella*.

7. The vaccine according to claim 1 wherein the mucosal surfaces are selected from the gastrointestinal tract, respiratory tract, urinary tract, auditory tract or conjuctiva.

8. The vaccine according to claim 6 wherein the *Shigella* is selected from *S. flexneri* 2a or *Shigella sonnei*.

9. A process for inducing secretory immunoglobulins on mucosal surfaces comprising administering to a subject the vaccine of claim 1.

10. The process of claim 9 wherein the administration involves multiple dosages of the vaccine over time.

11. The process of claim 9 wherein the infectious or toxic disease is a mucosal disease.

12. The process of claim 11 wherein the mucosal disease is a diarrheal disease.

13. The process of claim 11 wherein the mucosal disease is a meningococcal infection.

14. The process of claim 11 wherein the mucosal disease is a gonococcal infection.

15. A process for inducing immunoglobulins comprising administering to a subject the vaccine of claim 1.

16. The process of claim 15 wherein the administration involves multiple dosages of the vaccine over time.

17. The process of claim 15 wherein the infectious or toxic disease is a mucosal disease.

18. The process of claim 17 wherein the mucosal disease is a diarrheal disease.

19. The process of claim 17 wherein the mucosal disease is a meningococcal infection.

20. The process of claim 17 wherein the mucosal disease is a gonococcal infection.

* * * * *

UNITED STATES PATENT AND TRADEMARK OFFICE
CERTIFICATE OF CORRECTION

| | | |
|---|---|---|
| PATENT NO. | : 7,112,332 B1 | Page 1 of 1 |
| APPLICATION NO. | : 07/958426 | |
| DATED | : September 26, 2006 | |
| INVENTOR(S) | : George H. Lowell | |

It is certified that error appears in the above-identified patent and that said Letters Patent is hereby corrected as shown below:

Column 10
Lines 13-14, claim 2 should read as -- 2. The vaccine according to claim 1 wherein the lipopolysaccharide is derived from a gram negative bacteria. --.

Lines 15-16, claim 3 should read as -- 3. The vaccine according to claim 1 further comprising an antigen derived from a microorganism. --.

Lines 21-22, claim 6 should read as -- 6. The vaccine according to claim 2 wherein the gram negative bacteria is a *Shigella* species. --.

Lines 23-25, claim 7 should read as -- 7. The vaccine according to claim 2 wherein the mucosal surfaces are from the gastrointestinal tract, respiratory tract, urinary tract, auditory tract or conjuctiva. --.

Line 29, "mucosal surfaces comprising administering to a subject" should read as -- mucosal surfaces comprising orally or intranasally administering to a subject --.

Lines 41-42, "comprising administering to a subject" should read as -- comprising orally or intranasally administering to a subject --.

Lines 45-46, claim 17 should read as -- 17. The process of claim 15 wherein the administration affords an immune protective response to a mucosal disease. --.

Signed and Sealed this

Thirteenth Day of October, 2009

David J. Kappos
*Director of the United States Patent and Trademark Office*